(12) United States Patent
Vesper

(10) Patent No.: US 11,779,221 B2
(45) Date of Patent: Oct. 10, 2023

(54) APPARATUS, METHOD AND STORAGE MEDIUM FOR LUMEN CURVE SIMPLIFICATION FOR EDITING IN ONE OR MORE IMAGES, SUCH AS IN OPTICAL COHERENCE TOMOGRAPHY IMAGES

(71) Applicant: Canon U.S.A., Inc., Melville, NY (US)

(72) Inventor: Andrew Frank Vesper, Townsend, MA (US)

(73) Assignee: Canon U.S.A., Inc., Melville, NY (US)

( * ) Notice: Subject to any disclaimer, the term of this patent is extended or adjusted under 35 U.S.C. 154(b) by 62 days.

(21) Appl. No.: 17/351,906

(22) Filed: Jun. 18, 2021

(65) Prior Publication Data

US 2022/0400954 A1 Dec. 22, 2022

(51) Int. Cl.
*G01J 9/02* (2006.01)
*A61B 5/00* (2006.01)
(Continued)

(52) U.S. Cl.
CPC .......... *A61B 5/0066* (2013.01); *A61B 5/0084* (2013.01); *A61B 5/02007* (2013.01);
(Continued)

(58) Field of Classification Search
CPC . A61B 5/0066; A61B 5/0084; A61B 5/02007; G01B 9/02091; G06T 7/0012; G06T 2207/10101
See application file for complete search history.

(56) References Cited

U.S. PATENT DOCUMENTS

| | | |
|---|---|---|
| 6,565,514 B2 | 5/2003 | Svanerudh et al. |
| 7,978,916 B2 | 7/2011 | Klingensmith et al. |

(Continued)

FOREIGN PATENT DOCUMENTS

| | | |
|---|---|---|
| JP | 2001034774 A | 2/2001 |
| JP | 2019088772 A | 6/2019 |

(Continued)

OTHER PUBLICATIONS

Papadogiorgaki M, Mezaris V, Chatzizisis YS, Giannoglou GD, Kompatsiaris I. Image analysis techniques for automated IVUS contour detection. Ultrasound Med Biol. Sep. 2008;34(9):1482-98. doi: 10.1016/j.ultrasmedbio.2008.01.022. Epub Apr. 24, 2008. PMID: 18439746. (Year: 2008).*

(Continued)

*Primary Examiner* — Uzma Alam
*Assistant Examiner* — Jonathon Cook
(74) *Attorney, Agent, or Firm* — Canon U.S.A., Inc. IP Division

(57) ABSTRACT

A method for reproducing a lumen curve to a given tolerance in at least one image in optical coherence tomography (OCT). Examples of applications include imaging, evaluating and diagnosing biological objects, such as, but not limited to, cardio applications, and being obtained via one or more optical instruments, such as, but not limited to, catheters. The method may include obtaining a set of original points of the curve that correspond to measurements from an optical imaging device. Filtering the set of original points using at least one criteria to obtain a subset of original points. The method may also include determining if the subset of original points is less than a predetermined threshold and adjusting the at least one criteria to increase an amount of original points included in the subset of original points when it is determined that the subset of original points is less than the predetermined threshold.

19 Claims, 7 Drawing Sheets

(51) Int. Cl.
 *A61B 5/02* (2006.01)
 *G01B 9/02091* (2022.01)
 *G06T 7/00* (2017.01)

(52) U.S. Cl.
 CPC ........ *G01B 9/02091* (2013.01); *G06T 7/0012* (2013.01); *G06T 2207/10101* (2013.01)

(56) References Cited

U.S. PATENT DOCUMENTS

| | | |
|---|---|---|
| 8,493,567 B2 | 7/2013 | Inoue |
| 9,138,147 B2 | 9/2015 | Schmitt et al. |
| 10,621,748 B2 | 4/2020 | Kunio et al. |
| 2014/0276011 A1 | 9/2014 | Schmitt et al. |
| 2015/0320317 A1 | 11/2015 | Furuichi et al. |
| 2017/0301084 A1* | 10/2017 | Gopinath ........... A61B 5/02007 |
| 2019/0374109 A1 | 12/2019 | Wu et al. |

FOREIGN PATENT DOCUMENTS

| | | | |
|---|---|---|---|
| WO | WO-2014055923 A2 * | 4/2014 | .......... A61B 5/0066 |
| WO | 2014/115182 A1 | 7/2014 | |

OTHER PUBLICATIONS

U.S. Appl. No. 62/798,885, filed Jan. 30, 2019.
U.S. Appl. No. 63/046,495, filed Jun. 30, 2020.
U.S. Appl. No. 17/098,042, filed Nov. 13, 2020.
Hyungjun Park, et al., Error-Bounded B-Spline Curve Approximation Based on Dominant Point Selection, Proceedings of the Computer Graphics, International Conference on Computer Graphics, Imaging and Visualization, Beijing, CN, Jul. 26, 2005, XP010843563.
Gurmeric Serhan, et al., A New 3-d Automated Computational Method to Evaluate In-Stent Neointimal Hyperplasia in In-Vivo Intravascular Optical Coherence Tomography Pullbacks, Med Image Comput Comput Assist Interv. Part II, 2009, XP047462911.

* cited by examiner

APPARATUS, METHOD AND STORAGE MEDIUM FOR LUMEN CURVE SIMPLIFICATION FOR EDITING IN ONE OR MORE IMAGES, SUCH AS IN OPTICAL COHERENCE TOMOGRAPHY IMAGES

FIELD OF THE DISCLOSURE

The present disclosure relates generally to the field of optical imaging and more particularly to one or more optical apparatuses, systems, methods, such as, but not limited to, fiber optic catheters, endoscopes and/or optical coherence tomography (OCT) and/or fluorescence apparatuses and systems, and methods and storage mediums, for use with same, to achieve lumen curve simplification for editing of images, such as OCT or other (e.g., intravascular ultrasound (IVUS), other lumen image(s), etc.) images. Examples of such applications include imaging, evaluating and diagnosing biological objects, such as, but not limited to, for cardio, and being obtained via one or more optical instruments, such as, but not limited to, catheters.

BACKGROUND OF THE DISCLOSURE

Fiber optic catheters have been developed to access internal organs. For example in cardiology, OCT has been developed to see depth resolved images of vessels with a catheter. The catheter, which may include a sheath, a coil and an optical probe, may be navigated to a coronary artery. A lumen may refer to the interior of a blood vessel, such as the central space in an artery, vein or capillary through which blood flows.

OCT is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency.

In order to obtain a lumen curve for editing, geometric measurements of blood vessels from OCT images are detected. The hardware that is used for OCT imaging corresponds to the quantity of control points on the lumen curve. In some cases, the type of catheter (hardware) used may result in a set of approximately 500 control points. A curve consisting of 500 control points will include significantly more control points than are necessary to reproduce the curve to a given tolerance. For example, if the curve is close to a perfect circle, only 8 points are needed to reproduce the curve using a cubic spline technique. Since the lumen is the inside space of a tubular structure, the curve may resemble more of a circle. Using 500 control points for the lumen could be very noisy for editing, the set of 500 control points is significantly more than is needed to reproduce the lumen curve for editing and can be an arduous process due to the many control points for the lumen.

Image processing approaches for lumen curve detection will sometimes produce erroneous results due to noise in the system. A known method to improve the accuracy of the detected lumen curve requires a user select a particular control point to edit. Two other control points are automatically chosen based on the user selected control point to form a region to manipulate. As the selected control point is moved, new control points are computed in the region. This process has two potential issues. First, the number of control points could only be reduced, never added to. After a number of these editing operations, the lumen could become overly simplified. Second, the chosen region could be shorter or longer than desired, making the lumen curve difficult to edit.

There are currently known methods intended to simplify the display of computer-generated paths, consisting of straight and curved line segments. The output also consists of straight and curved line segments, with the curved segments described as parametric curves, which are difficult for a user to edit. An additional drawback is that the output contains interpolated points, which may be an issue for fidelity to the original curve.

Accordingly, there is a need in the art for producing the fewest control points feasible or useful and, with each iteration, changing a criteria to select a greater number of points until an acceptable number of points is determined and the difference between an input curve and an output curve is less than a predetermined threshold to simplify a lumen curve for editing.

SUMMARY

The present disclosure includes repeated selection of control points and checking a tolerance at various steps in the process. A control point selection criteria is initialized to produce the fewest points feasible. Thus, instead of starting with a large set of control points, the present disclosure aims to begin with the fewest points that are useful and, with each iteration, changing the criteria to select a greater number of points. The iteration continues until the number of control points are acceptable and the difference between the input and output curves is less than a given tolerance. This process of repeated selection of control points and checking the tolerance at each step may occur in real-time based on a single frame of an OCT image. Accurately reproducing a lumen curve using a single OCT frame helps to improve overall object or target, such as a vessel, measurement accuracy, including for post processing as well as enhanced lumen curve simplification for editing.

In one or more embodiments of the present disclosure, a method for reproducing a curve to a given tolerance in at least one image is provided. The given tolerance is a threshold used to determine whether the difference between an input curve and an output curve is within an acceptable range. The method includes obtaining a set of original points of the curve that correspond to measurements from an optical imaging device. In this regard, the set of original points are significantly more points than are needed for reproducing the original curve of at least one image such as an OCT image obtained from an OCT imaging modality. The set of original points may directly correspond to a type of catheter used for obtaining the original curve of an OCT image. The method may continue with filtering the set of original points using at least one criteria to obtain a subset of original points. The criteria being a determining factor for how many original points are included in the subset of original points. Thus, manipulating the criteria may allow for increasing a quantity of original points to be selected and included in the subset of original points from the original curve. The method also includes adjusting at least one criteria to increase an amount of original points included in the subset of original points. If the subset of original points satisfies the predetermined threshold, the criteria is not adjusted. However, if the subset of original points is less than the predetermined threshold, the criteria is adjusted in order to increase the quantity of original points to be selected for the subset. At least one criteria is adjusted until it is determined that the subset of original points is equal to or greater than the predetermined threshold.

In accordance with one or more embodiments of the present disclosure, apparatuses and systems, and methods and storage mediums for lumen reproduction to a given tolerance in one or more images may operate to characterize biological objects, such as, but not limited to, blood, mucus, tissue, etc.

It should be noted that one or more embodiments of the lumen reproduction to a given tolerance in one or more images of the present disclosure may be used in other imaging systems, apparatuses or devices, where images are formed from signal reflection and scattering within tissue sample(s) using a scanning probe. For example, IVUS images may be processed in addition to or instead of OCT images.

One or more embodiments of the present disclosure may be used in clinical application(s), such as, but not limited to, intravascular imaging, atherosclerotic plaque assessment, cardiac stent evaluation, balloon sinuplasty, sinus stenting, arthroscopy, ophthalmology, ear research, veterinary use and research, etc.

In accordance with at least another aspect of the present disclosure, one or more technique(s) discussed herein may be employed to reduce the cost of at least one of manufacture and maintenance of the one or more apparatuses, devices, systems and storage mediums by virtue of the efficient techniques to cut down cost of use/manufacture of such apparatuses, devices, systems and storage mediums.

Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION

One or more devices/apparatuses, optical systems, methods and storage mediums for lumen curve simplification for editing are disclosed herein.

Figure 1:
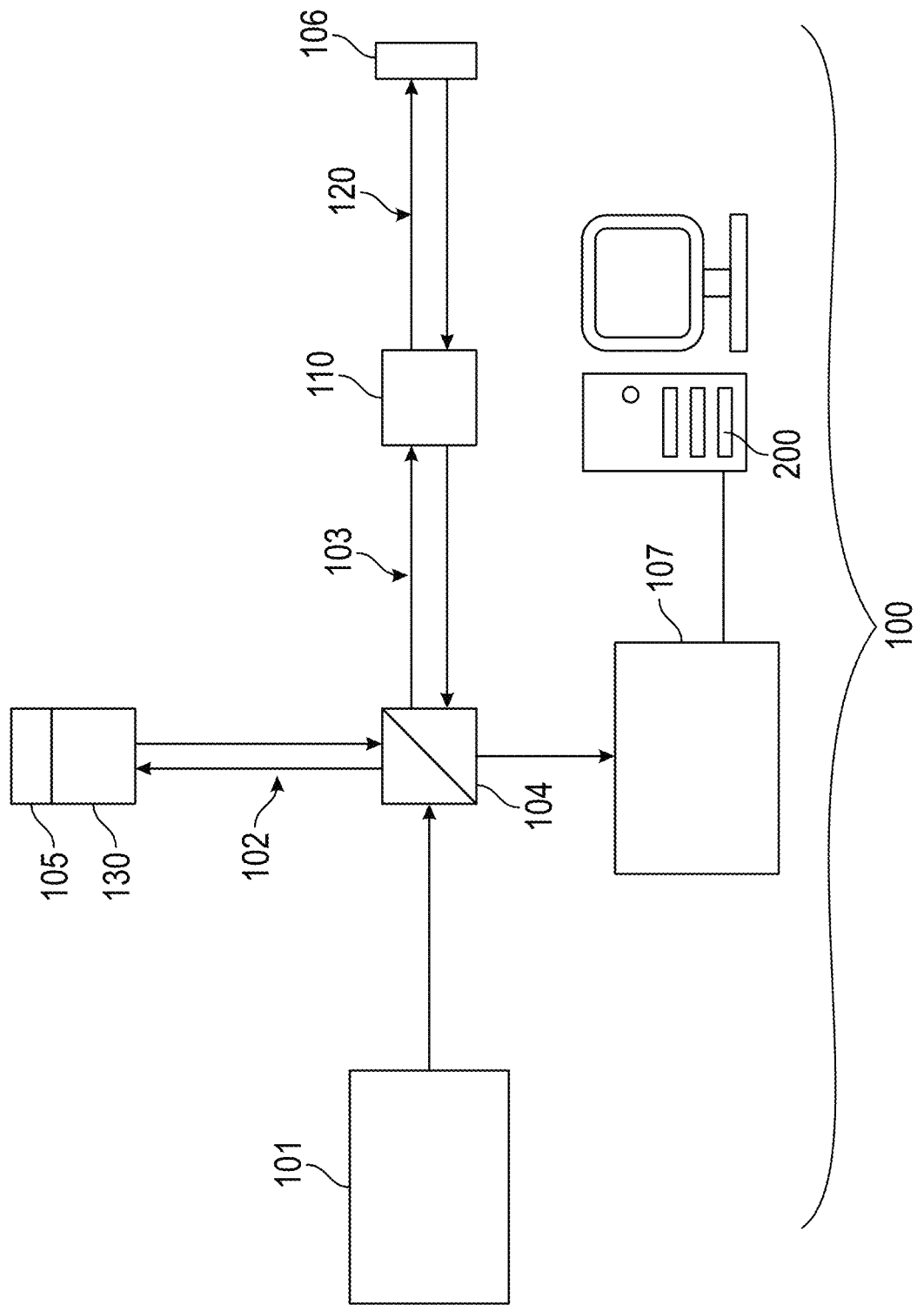
FIG. 1 is a schematic diagram of an Optical Coherence Tomography (OCT) imaging system for obtaining OCT images to be simplified for editing in accordance with one or more aspects of the present disclosure.

Lumen curve simplification for editing allows a user to edit an image or images obtained from an OCT imaging system. Turning now to the details of the figures, FIG. 1 shows an OCT system 100 (as referred to herein as "system 100" or "the system 100") which operates to utilize an OCT technique, including, but not limited to, one or more embodiments of lumen curve simplification for editing discussed herein, in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130, and, in one or more embodiments, the phase shift device or unit may be omitted. In one or more embodiments, the system 100 may include a patient interface device or unit ("PIU") no and a catheter 120, and the system 100 may interact with a sample or target 106 (e.g., via the catheter 120 and/or the PIU 110). In one or more embodiments, the system 100 includes an interferometer, or an interferometer is defined by one or more components of the system 100, such as, but not limited to, at least the light source 101, the reference arm 102, the sample arm 103, the splitter 104 and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample or target 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit) no and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 200, 200' (shown in FIG. 7 or FIG. 8, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which is then used to for spectral encoding of spatial information. The light source 101 may be fiber coupled or may be free space coupled to the other components of the system or systems discussed herein, such as, but not limited to, the system 100, the system 100', the system 100", the system 100''', etc.

Figure 2:
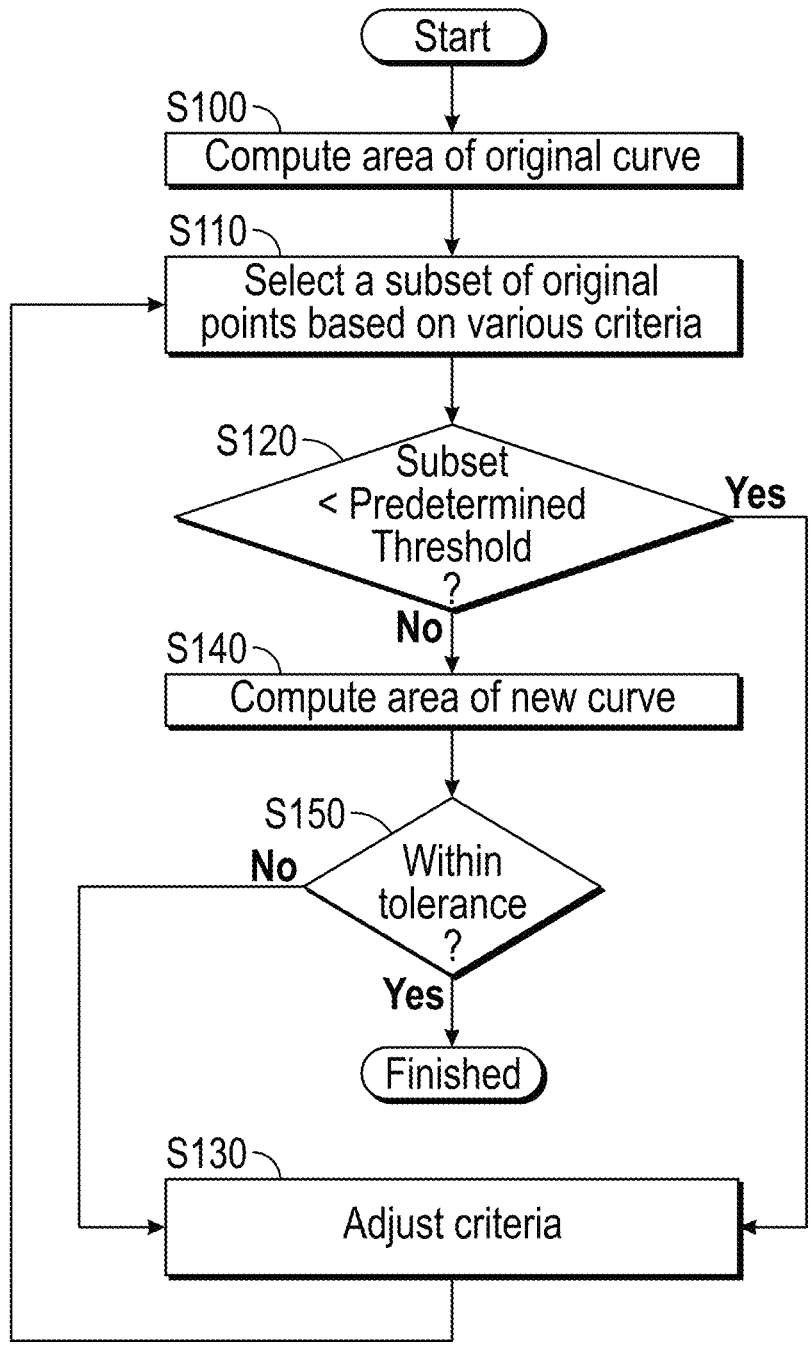
FIG. 2 is a flowchart showing an embodiment of a method for reproducing a lumen curve in at least one image in accordance with one or more aspects of the present disclosure.

FIG. 2 shows a flowchart for lumen curve simplification from measurements obtained using a catheter 120 of the OCT system 100. The set of control points associated with a lumen curve are dependent upon the type of hardware used. Throughout the present disclosure a catheter that results in a set of approximately 500 control points is used. However, this is merely by way of example and other types of catheters, probes, scopes or hardware may be used that result in more or less than 500 control points. In other words, the 500 control points used throughout the present disclosure is representative of one type of catheter. Various quantities of control points may be used as a starting point for lumen curve simplification for editing in accordance with the present disclosure. The quantity of control points are dependent on the hardware used with the OCT system 100.

A lumen curve obtained from the OCT system 100 using a catheter 120 may consist of a set 500 control points for example. Unfortunately, the set of 500 control points is significantly more than necessary for reproducing the lumen curve to a given tolerance. Furthermore, when a user selects a particular control point from the set of 500 control points for editing, two other control points are automatically chosen to form a region to be manipulated. As the selected control point is moved by the user during editing, new control points are computed in the region. This method of lumen may result in fewer control points in the manipulated region. After a few editing operations by the user, the lumen curve could become overly simplified due to the reduced number of control points. Additionally, the chosen region for editing may be shorter or longer than the user desires which makes it more difficult for the user to edit.

A better method for lumen editing in accordance with the present disclosure includes the steps implemented in the flowchart of FIG. 2. The steps shown in FIG. 2 may reduce the processing burden associated with a user editing a lumen curve with an excessive amount of control points.

In step S100 of FIG. 2, the area of the original curve is computed. The original curve is the curve that is made up of the set of approximately 500 control points. It is important to note that the 500 control points is merely an example of the control points of the curve. The quantity of control points may vary based on several factors including the type of catheter or probe that is being used. The 500 control points is merely by way of example and not meant to limit the scenario in which the method of the present disclosure may be applied. Subsequent to the area of the original curve being computed in step S100, the excessive amount of control points, in this example, 500, is filtered to a significantly reduced count for the control points in step S110. In particular, in step S110, the 500 control points are filtered by selecting a subset of the original 500 points based on various criteria. In step S110, it is important that the filtering of the control points is significantly reduced such that the subset starts at a quantity of original points that may be less than a minimum quantity of points needed to reproduce the lumen curve accurately.

The subset of original points may be obtained based on various criteria. The various criteria may be point-to-point distance, local curvature, quality of measurement, etc. by way of example. Other criteria not explicitly disclosed herein may be used in accordance with the present disclosure. The selection of measures and criteria should be determined by the specific needs of the particular implementation (optical imaging device). The goal being to drastically filter the original set of control points so that when a user wants to edit the lumen curve, the total amount of control points is low (a subset of control points), thereby reducing the processing burden and time required to accurately reproduce the lumen curve.

Once the original set of control points (500 in this example) is significantly reduced in step S110 by selecting a subset of original points based on at least one criteria from the various criteria, it is determined whether the quantity of control points associated with the subset of original points exceeds a predetermined threshold in step S120. The predetermined threshold is a minimum total quantity of control points that the subset of original points should be equal to or greater than to accurately reproduce the lumen curve. The predetermined threshold is used to ensure that the criteria used to drastically reduce the quantity of original points does not result in too few points for the subset of original points. If there are too few control points, it will be difficult to accurately reproduce the lumen curve. The predetermined threshold may be determined based on specific needs. For example, a cubic-spline curve technique, requires 8 points which will allow for perfect circles. Other curve types may have different needs and therefore differing requirements for the number of control points. A somewhat higher number might help a user with manual editing, although any manual editing process should allow for insertion of new points.

If it is determined in step S120, that the selected subset of original points is less than the predetermined threshold (YES in step S120), the method for reproducing the curve continues to step S130 to adjust the criteria used to select the subset of original points in step S110. The criteria is adjusted to allow for the selection of more control points when selecting the subset of original points. Then the new subset of original points returns to step S120 to determine whether the subset of original points satisfies the predetermined threshold. Thus, steps S110, S120 and S130 are an iterative process that continuously loops until the predetermined threshold in step S120 is satisfied. Only when the predetermined threshold is satisfied may the method for reproducing the lumen curve in accordance with an aspect of the present disclosure continue. The advantage of this process is to essentially start with a minimum amount of control points (the subset of original points) and iteratively add to the subset of original points to be used to reproduce the lumen curve to ensure that when the user edits the lumen curve, the processing burden is minimized and the time required to reproduce the lumen is curve is reduced. Instead of starting from an editing position where a set of 500 control points are to be considered, the total quantity of control points to be considered during the editing process in accordance with the present disclosure might only include 8, 12 or 20 control points by way of example. A significantly lower amount of control points than the original set of 500 points.

In step S120, if it is determined that the selected subset of original points satisfies the predetermined threshold (NO in step S120), the method for reproducing the lumen curve continues to step S140. A NO result in step S120 is a determination that the selected subset of original points satisfies the predetermined threshold and the criteria does not need to be adjusted. In step S140, the area of the new curve is computed. The new curve is the curve that is based on the selected subset of original points. Whereas, the original curve is based on the set of 500 control points in this example. The area of the new curve is based on the drastically reduced selected subset of control points that is computed in step S140. It is then determined in step S150 whether the new curve is within a given tolerance. If the new curve is not within the given tolerance, the new lumen curve does not sufficiently replicate the original lumen curve that was based on the set of 500 control points and therefore is not used for lumen curve editing by a user. When it is determined that the new curve is not within the given tolerance (NO in step S150), the method for lumen curve reproduction proceeds to step S130 in order to adjust the criteria to allow for more control points to be selected in step S110 when selecting the subset of original points.

The given tolerance ensures that the new curve adequately replicates the original curve while keeping the total quantity of control points associated with the subset of original points to a minimum or at least significantly reduced from the original quantity of control points associated with the original curve. Steps S150, S130 and S110 form an iterative process that guarantees the reproduced lumen curve based on the selected subset of original points satisfies the given tolerance while minimizing the total quantity of original points used with the subset of original points. Alternatively, in step S150, if it determined that the area of the new curve satisfies the given tolerance (YES in step S150), then the method for reproducing the lumen curve may be terminated.

The given tolerance may be based on area, perimeter, root-mean-square of point-to-point differences, or whatever else a specific implementation requires. The given tolerance test must report success once the full set of points are selected to guarantee that the algorithm will terminate. Adjusting the criteria should be designed to keep increasing the number of control points up to the full list of points of the original curve. The adjustment to the criteria does not need to be strictly monotonic, but the trend must be to include more control points, otherwise, the algorithm is not guaranteed to terminate.

Figure 3:
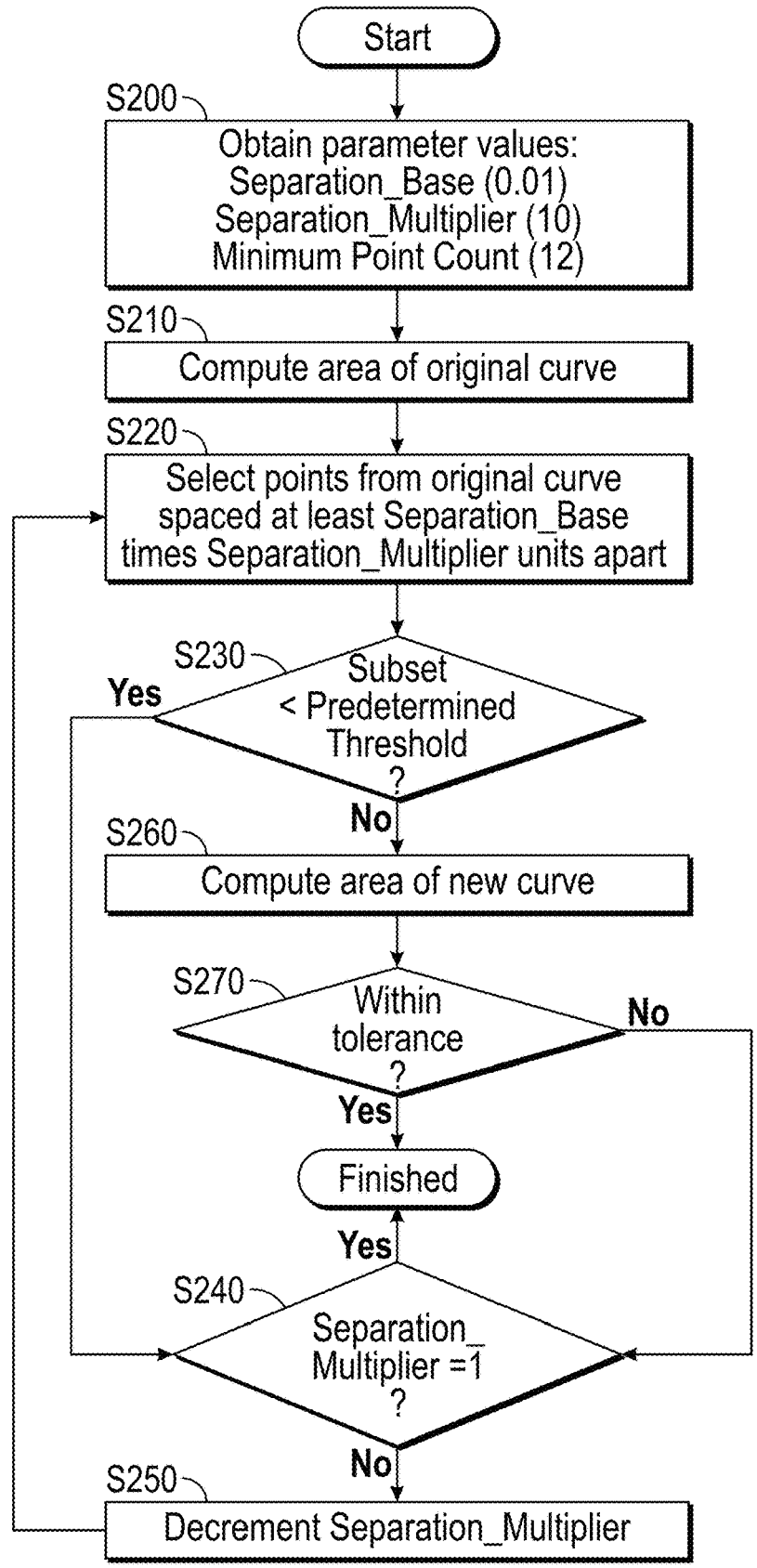
FIG. 3 is a flowchart of a second embodiment of a method for reproducing a lumen curve for editing in at least one multi-modality OCT (MMOCT) image in accordance with one or more aspects of the present disclosure.

In accordance with at least one aspect of the present disclosure and as aforementioned, one or more methods for lumen curve simplification for editing of OCT images are provided herein. FIG. 3 illustrates a flow chart of a second embodiment of a method for lumen curve simplification for editing of MMOCT image(s). Preferably, the method may initiate by obtaining parameter values in step S200. In this embodiment of the present disclosure, the parameter values are used to filter the set of original control points to a significantly reduced subset of control points associated with an original curve from an MMOCT image. The parameter values that are obtained include a Separation_Base, a Separation_Multiplier and Minimum Point Count. The Separation_Base value in parenthesis is 0.01 and is a sample value that may be used. The sample value of 0.01 is for exemplary purpose and other values for the Separation_Base may be used in accordance with the present disclosure. The Separation_Multiplier value in parenthesis is 10 and is a sample value that may be used. The sample value 10 is for exemplary purpose and other values for the Separation_Multiplier may be used in accordance with the present disclosure. The minimum point count includes a sample value of 12 for exemplary purposes and other values for the minimum point count may be used in accordance with the present disclosure.

Next, in step S210, the area of the original curve is computed based on the set of original points. Similar to the embodiment of FIG. 2, the set of original points in this embodiment may also include 500 control points depending on the catheter 120 used with the OCT system 100. In step S220, a subset of original control points are selected from the original curve. The subset of original control points are spaced at least the Separation_Base multiplied by the Separation_Multiplier units apart. In other words, step S220 is a filtering step to significantly reduce the set of original points into the subset of original points for reproducing the lumen curve. In step S220, the subset of original points are selected from the original curve using the two obtained parameter values. Namely, the Separation_Base and the Separation_Multiplier. In step S220, the original set of control points are selected from the original curve spaced at least a Separation_Base multiplied by a Separation_Multiplier units apart. For example, if the Separation_Base is 0.01 and the Separation_Multiplier is 10, the set of original points selected from the original curve are spaced at least 0.1 units apart. Thus, if original points from the set of original points are spaced closer than 0.1 units apart, those original points are not included in the subset of original points. Using the Separation_Base times the Separation_Multiplier to filter the set of original points should result in a subset of original points that is significantly reduced.

Still referring to FIG. 3, the next step S230 determines whether the point count is less than a minimum point count. The minimum point count being one of the parameter values obtained in step S200. The minimum point count is a predetermined threshold value for ensuring that the subset of original points is equal to or greater than a minimum amount of original points needed to reproduce the lumen curve. In step S230, it is determined whether the selected subset of original points satisfies the minimum point count parameter value. If it is determined in step S230 that the point count of the selected subset of original points is less than 12 (YES in step S230), the method for reproducing the lumen curve continues to step S240 to determine whether the Separation_Multiplier is equal to 1. The Separation_Multiplier that is used in this example is 10 from the obtained parameter values in step S200, therefore the Separation_Multiplier is not equal to 1 (NO in step S240). Then, the method for reproducing the lumen curve proceeds to step S250 which requires that the Separation_Multiplier is decremented. For illustrative purposes, the Separation_Multiplier is decremented by one unit. However, the Separation_Multiplier may be decremented by more than one unit and is merely for exemplary purposes. In this example, if the Separation_Multiplier is decremented by one, the new Separation_Multiplier is 9 instead of 10 and the method for reproducing the lumen curve returns to step S220 to select a subset of original points using the new Separation_Multiplier. For this example, the points must now be spaced 0.09 units apart instead of 0.1 units apart because the Separation_Multiplier*Separation_Base (0.01)*(9)=0.09. The subset of original points selected from the original curve are spaced at least 0.09 units apart, because the points are now spaced closer together than when the Separation_Multiplier was 10, the subset of original points will be greater. The iterative process is continued until either the minimum point count is satisfied (NO in step S230) or the Separation_Multiplier is equal to 1 (YES in step S240). This iterative process ensures that either the minimum point count threshold is met or that the Separation_Multiplier is equal to 1. When the Separation_Multiplier is equal to 1, the method for reproducing the lumen curve may be terminated.

Steps S220, S230, S240 and S250 form an iterative loop that guarantee the minimum point count parameter value is satisfied or that the Separation_Multiplier is equal to 1. This ensures that the algorithm terminates eventually. It should be noted that when the Separation_Multiplier is equal to 1 there will be a large quantity of control points associated with the subset of original points. Preferably, the minimum point count is satisfied prior to the Separation_Multiplier equaling 1.

Alternatively, when it is determined that the point count of the subset of original points selected are spaced at least by the Separation_Base multiplied by the Separation_Multiplier and satisfy the minimum point count (NO in step S230), then the method for reproducing the lumen curve continues to step S260. The minimum point count in this example is 12. Thus, the subset of original points that are selected from the original curve and spaced apart at least by the Separation_Base multiplied by the Separation_Multiplier must equal 12 or greater to proceed to step S260. In step S260, the area of a new curve is computed. The new curve is based on the subset of original points selected from the original curve. In this example the area of the new curve is based off of at least the minimum point count which is at least 12 points. The area of the new curve is computed in order to determine if the new curve is within a given tolerance when compared with the original curve. In step S270, it is determined whether the new curve is within the given tolerance. If the area of the new curve is within the given tolerance (YES in step S270), the method for reproducing the lumen curve is terminated.

If the area of the new curve is not within a given tolerance (NO in step S270), the method for reproducing the lumen curve proceeds to step S240 to determine whether the Separation_Multiplier is equal to 1. If the Separation_Multiplier is not equal to 1, the method continues to step S250 by decrementing the Separation_Multiplier. Decrementing the Separation_Multiplier will result in a new subset of original points from the original curve that are spaced even closer together, which will result in more control points and lead to an area of a new curve that is closer or within the given tolerance. Steps S270, S240, S250 and S220 form an iterative loop that guarantees that the area of the new curve is within the given tolerance or the Separation_Multiplier is equal to 1. In most scenarios the area of the new curve will satisfy the given tolerance prior to the Separation_Multiplier equaling 1.

Figure 4B:
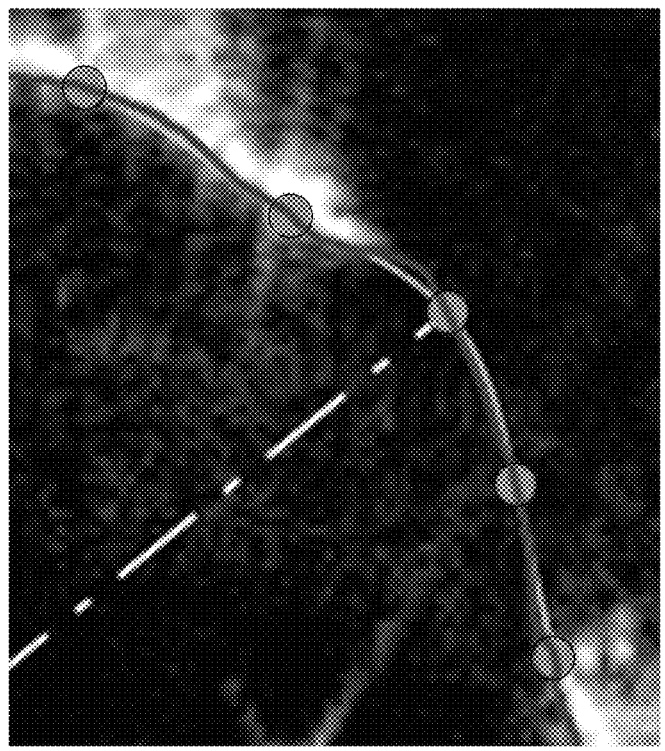
FIG. 4B is a zoomed-in image of the original cubic-spline curve from FIG. 4A in accordance with one or more aspects of the present disclosure.
Figure 4A:
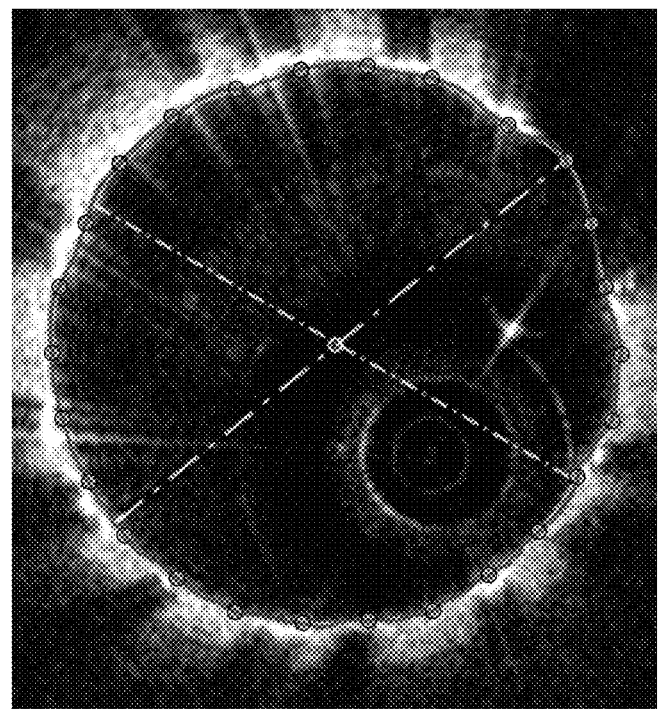
FIG. 4A is an image generated from a cubic-spline technique in accordance with one or more aspects of the present disclosure.

Referring now to FIG. 4A, an OCT image of a lumen curve is shown. The original lumen curve is shown in the darker shade curve which is made up of the set of original points that total approximately 500 control points in the exemplary sample. The darker shade curve is shown on top of the lighter shade point-reduced curve with gray dots showing the location of the output points. The gray dots are representative of the points that make up the subset of original points. As shown in FIG. 4A, the reproduced curve closely resembles the original curve yet requires significantly less control points than the original curve. FIG. 4B shows a zoomed-in detail of the first image from FIG. 4A. The image from FIG. 4A shows the full curve while the image in FIG. 4B shows just a detailed portion of the curve from FIG. 4A. Once the curve is reproduced as shown in both FIGS. 4A and 4B, the curve may be manipulated by the user through a conventional editing method which allows for points to be added. This corrects the issue where the old lumen editing technique could only simplify the curve. With the method described above in accordance with the present disclosure, details to the reproduced lumen curve may be added instead of simplified. The editing method of the present disclosure may also delete points which ameliorates the issue of the effective region of manipulation in previous lumen editing technique.

Figure 5:
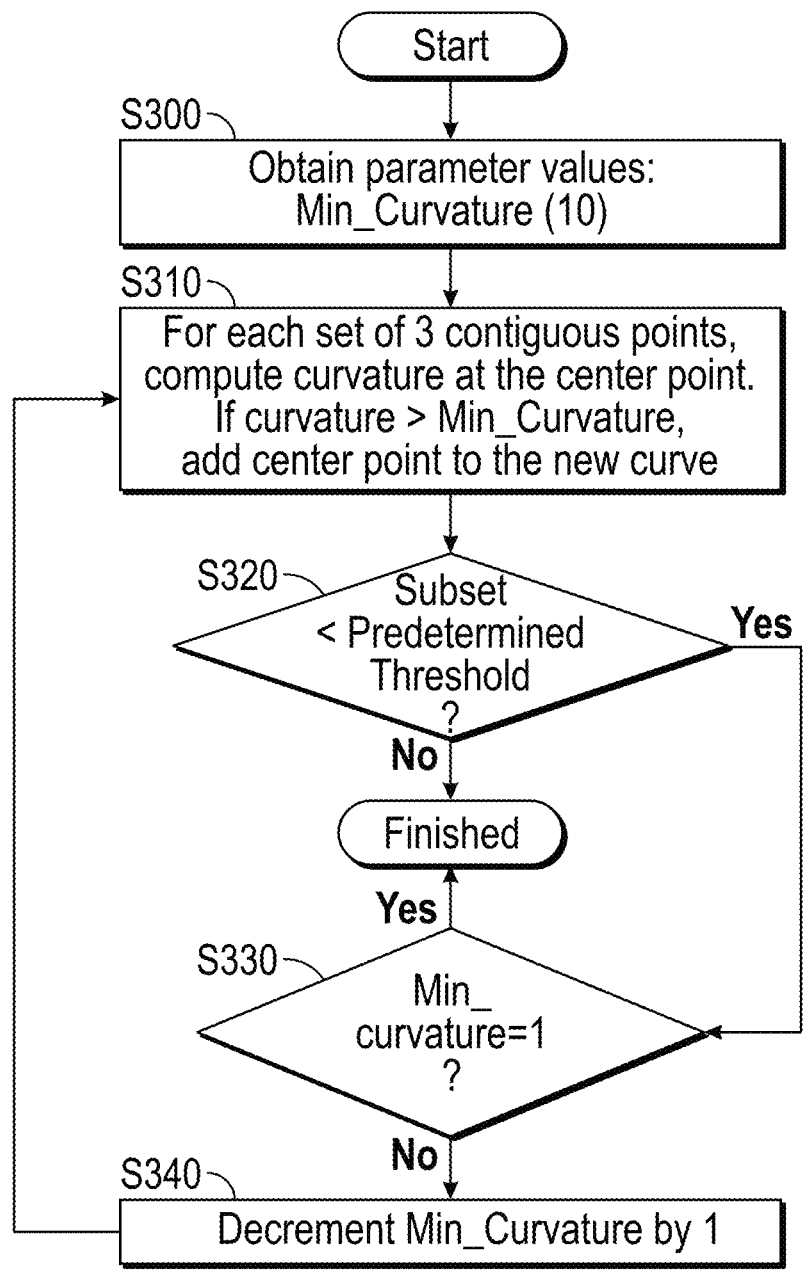
FIG. 5 is a flowchart of a third embodiment of a method for reproducing a lumen curve for editing in at least one MMOCT image using curvature as a criteria in accordance with one or more aspects of the present disclosure.

Referring now to FIG. 5, a third embodiment for reproducing a lumen curve to a given tolerance in at least one image in accordance with the present disclosure is described with respect to the various steps in the flowchart shown. In the third embodiment, curvature is used as a criteria to obtain a subset of original points that is preferred for lumen curve reproduction and editing. A method for reproducing a lumen curve to a given tolerance in at least one image may initiate by obtaining parameter values according to step S300. In step S300, the parameter value that are obtained is the minimum curvature (Min_Curvature) with a sample value of 10 in parenthesis. Although a sample value of 10 is shown, the minimum curvature may include a wide variety of values and the sample value provided is merely for exemplary purposes and meant to limit the values to be used for minimum curvature. After the parameter value is obtained (Min_Curvature) in step S300, the minimum curvature value is used in the next step S310.

In particular, step S310 a processor may compute the curvature at the center point for each set of 3 contiguous points from the original set of control points. If the curvature is greater than the minimum curvature (10 in this example), the center point from the 3 contiguous points is added to the new curve. Conversely, if the curvature is less than the minimum curvature, the center point from the 3 contiguous points is not included in the new curve. So although the center point was included in the original curve, it will not be included in the new curve. Step S310 effectively as a filter whereby the filtering process ensures that only a subset of original points that have a curvature greater than the minimum curvature (10 in this example) are added to the new curve.

Subsequently, in step S320 it is determined whether the subset of original points to be used for the new curve is less than a minimum threshold value for the quantity of control points to be used. If it is determined that the point count for the subset of original points satisfies the minimum threshold value (NO in step S320), the method for reproducing the lumen curve is terminated. Alternatively, if it is determined that the total point count for the subset of original points does not satisfy the minimum threshold value (YES in step S320), the method for reproducing a lumen curve proceeds to step S330 where it is determined whether the minimum curvature is equal to 1. If it is determined that the minimum curvature is equal to 1 (Yes in step S330), the method for reproducing the lumen curve using curvature as a criteria is terminated. Alternatively, if it is determined that the minimum curvature is not equal to 1 (NO in step S330), the method for reproducing a lumen curve with curvature as a criteria continues to step S340. In the example above, the minimum curvature started at a value of 10. So in a case where the quantity of control points associated with the subset of original points does not satisfy the minimum threshold, the minimum curvature is decremented in step S340. For example, if the minimum curvature is to be decremented by 1, the new minimum curvature value is 9. This ensures that more control points from the original set of control points are to be added to the new curve. This iterative process continues until the subset of original points satisfies the minimum threshold value or the minimum curvature is equal to 1. This ensures that the algorithm will terminate at some point while effectively determining a minimum quantity of control points to be used for the subset of original points for reproducing a lumen curve accurately. Steps S310, S320, S330 and S340 form an iterative loop to continuously add control points to the subset of original points until the minimum threshold value is satisfied or until the minimum curvature is equal to 1.

Figure 6:
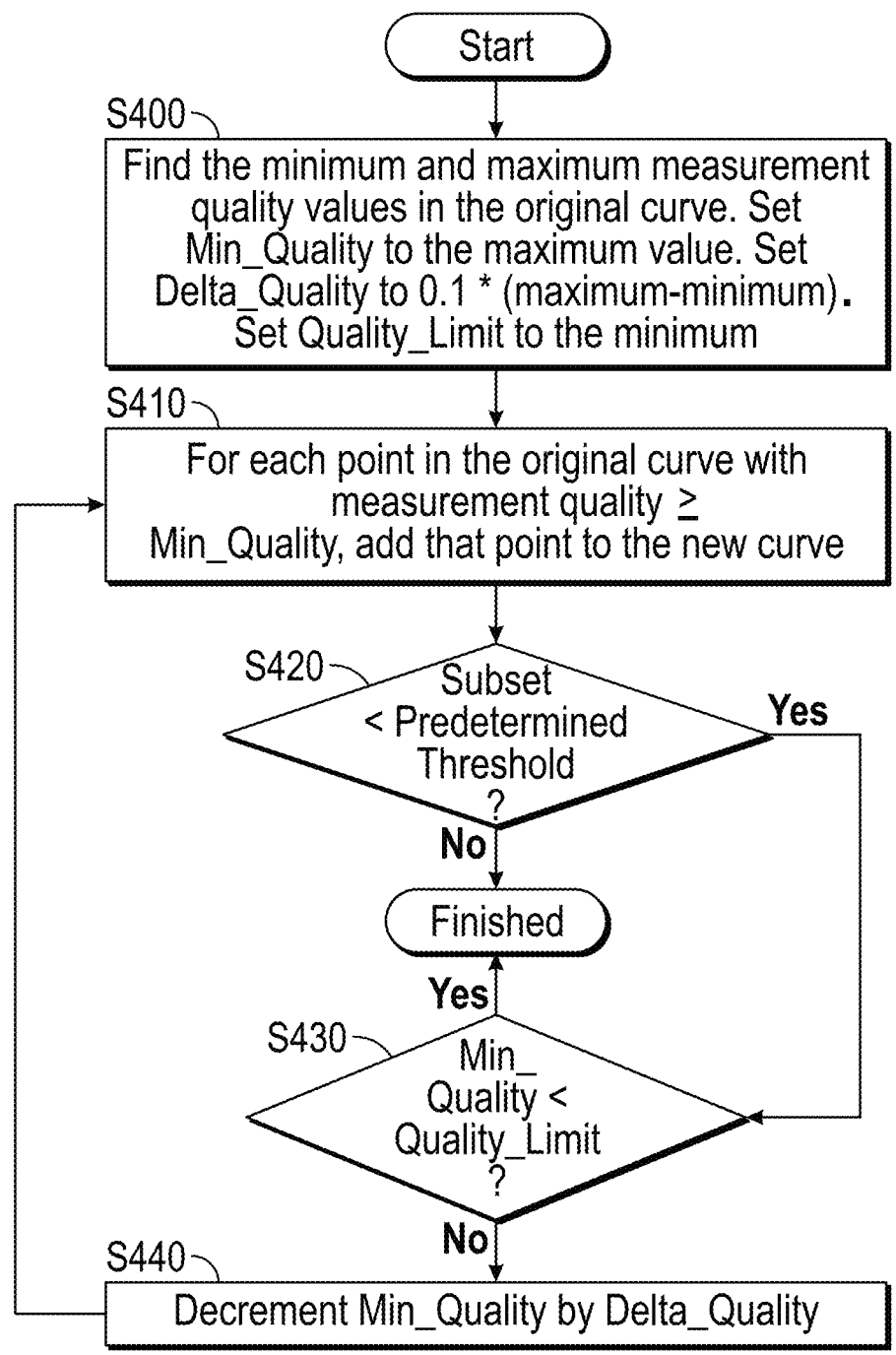
FIG. 6 is a flowchart of a fourth embodiment of a method for reproducing a lumen curve for editing in at least one MMOCT image using quality of measurement in accordance with one or more aspects of the present disclosure.

Referring now to FIG. 6, a fourth embodiment for reproducing a lumen curve in at least one image in accordance with the present disclosure is described with respect to the various steps in the flowchart shown. The fourth embodiment includes quality of measurement as a criteria for obtaining a subset of original points to be added to a new curve. In step S400, minimum and maximum measurement quality values are determined from the original curve. The minimum and maximum measurement quality values may range from any number between 0 and 100. The minimum and maximum measurement quality values make up a range of values for the quality of measurement criteria. In step S400, the minimum quality is set to the maximum value. When setting the minimum quality to the maximum value, this significantly reduces the set of original points that total approximately 500 to a drastically reduced quantity such as a subset of original points consisting of 6 points by way of example.

In step S400, a delta quality (Delta_Quality) is also set. The delta quality is used for changing the quality of measurement criteria if needed as will be described below. The delta quality is determined by multiplying 0.1*(maximum measurement quality value−minimum measurement quality value). If the measurement quality in the original curve is not well spread out between the minimum and the maximum measurement quality, the flowchart of FIG. 6 may return a new curve with too many points. This issue may be ameliorated by changing the delta quality to 0.01*(maximum measurement quality value−minimum measurement quality value) or some similar value to prevent too many points from being added to the new curve. The quality limit (Quality_Limit) is set in step S400 as well. The quality limit is set to the minimum measurement quality value. Thus, three parameter values are set in step S400 after finding the minimum and maximum measurement quality values in the original curve. The three parameter values include minimum quality, delta quality and quality limit.

Next in step S410, for each point in the original curve with a measurement quality greater than or equal to the minimum quality, those points are added to the new curve. Setting the minimum quality to the maximum measurement quality allows for a significant reduction in the total quantity of control points from the original curve that are added to the new curve. In other words, the set of original points from the original curve are significantly reduced to a subset of original points representing a new curve. Once a subset of original points is obtained, the method continues to step S420 to determine whether the subset of original points satisfies a minimum threshold value for the total quantity of control points associated with the subset of original points. If it is determined that the subset of original points satisfies the threshold value (NO in step S420), the method for reproducing the lumen curve using measurement quality as a criteria may terminate and the subset of original points are used to reproduce the lumen curve.

Alternatively, if it is determined that the subset of original points does not satisfy the minimum threshold value (YES in step S420), the method for reproducing the lumen curve using measurement quality as a criteria proceeds to step S430. In step S430, it is determined whether the minimum quality is less than the quality limit. If it is determined that the minimum quality is less than the quality limit (YES in step S430), the method for reproducing the lumen curve using measurement quality as a criteria is terminated. Alternatively, if the minimum quality is not less than the quality limit (NO in step S430), the method for reproducing the lumen curve using quality of measurement as a criteria continues to step S440. In step S440, the minimum quality is decremented by the delta quality and then the method for reproducing the lumen curve returns to step S410 to obtain an updated subset of original points using the decremented minimum quality. Using a minimum quality with a lower value allows for more control points to be included in the subset of original points. This iterative process continues until either the minimum point count threshold is satisfied for the subset of original points or the minimum quality is less than the quality limit. This iterative loop ensures that the algorithm ends as well as result in a reduced amount of control points for reproducing the lumen curve using quality of measurement as a criteria.

A computer, such as the console or computer 200, 200', may perform any of the aforementioned steps for any system being manufactured or used, including, but not limited to, system 100, system 100', system 100", system 100'", etc.

One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

In at least one embodiment, a computer, such as the console or computer 200, 200', may be dedicated to the control and the monitoring of the OCT devices, systems, methods and/or storage mediums described herein.

Figure 7:
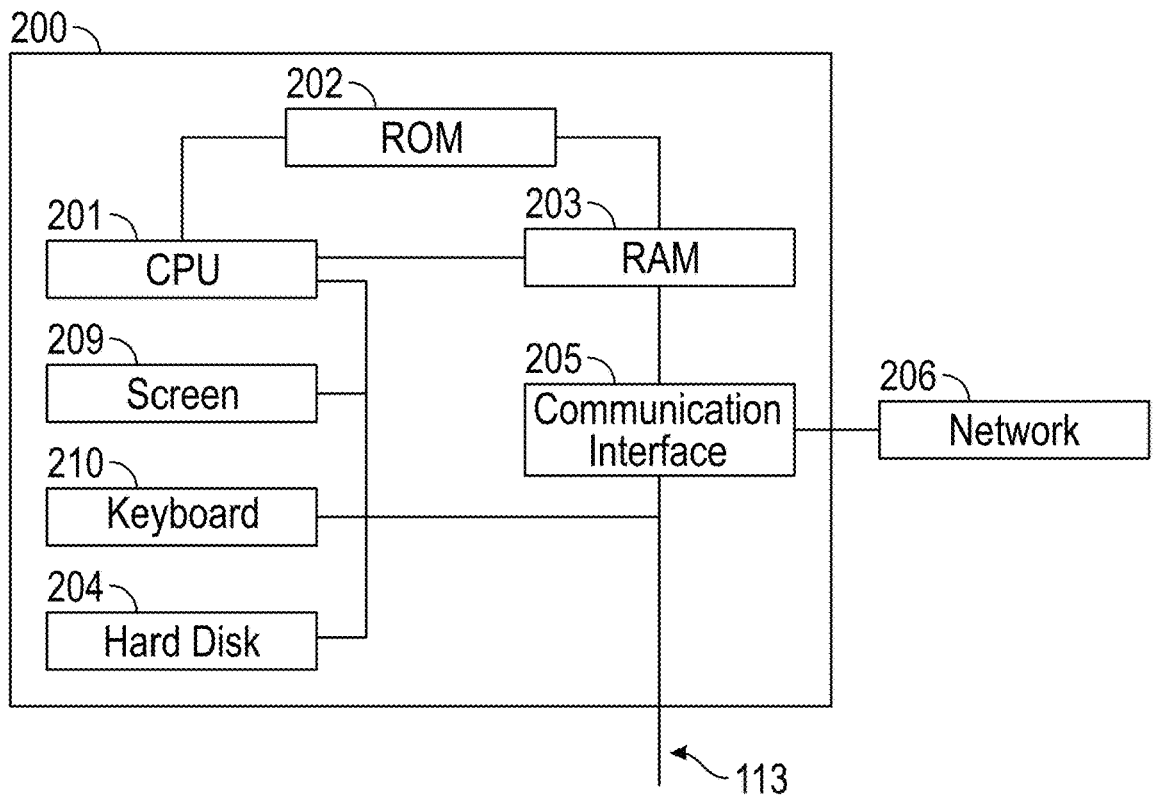
FIGS. 7 and 8 show a schematic diagram of an embodiment of a computer that may be used with one or more embodiments of at least one apparatus, system, method and/or storage medium, for performing a method of reproducing a lumen curve for editing in at least one image in accordance with one or more aspects of the present disclosure.

The electric signals used for imaging may be sent to one or more processors, such as, but not limited to, a computer 200 (see e.g., FIGS. 1, 7 and 8), a computer 200' (see e.g., FIG. 8), etc. as discussed further below, via cable(s) or wire(s), such as, but not limited to, the cable(s) or wire(s) 113 (see FIG. 7).

Figure 8:
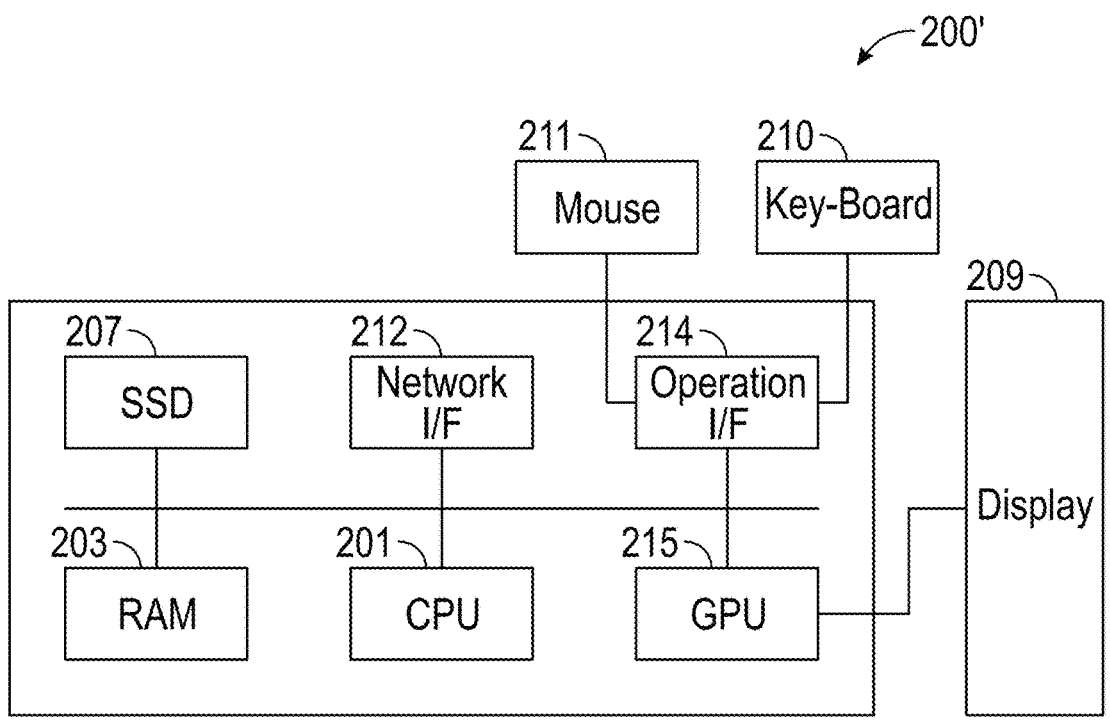

The I/O or communication interface 205 provides communication interfaces to input and output devices, which may include the light source 101, a RJ, a PM, an SM, unit 150, unit 112, a microphone, a communication cable and a network (either wired or wireless), a keyboard 210, a mouse (see e.g., the mouse 211 as shown in FIG. 8), a touch screen or screen 209, a light pen and so on. The Monitor interface or screen 209 provides communication interfaces thereto.

Any methods and/or data of the present disclosure, such as the methods for using and/or manufacturing a device, system or storage medium for use with same and/or method(s) for reproducing a lumen curve for editing, including in OCT image(s), as discussed herein, may be stored on a computer-readable storage medium. A computer-readable and/or writable storage medium used commonly, such as, but not limited to, one or more of a hard disk (e.g., the hard disk 204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 207 in FIG. 8), SRAM, etc.), an optional combination thereof, a server/database, etc. may be used to cause a processor, such as, the processor or CPU 201 of the aforementioned computer system 200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 200, the processor of computer 200', etc., as described above may be achieved utilizing suitable hardware, such as that illustrated in the figures. Functionality of one or more aspects of the present disclosure may be achieved utilizing suitable hardware, such as that illustrated in FIG. 7. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 201 (as shown in FIG. 7 or FIG. 8) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 200' is shown in FIG. 8. The computer 200' includes a central processing unit (CPU) 201, a graphical processing unit (GPU) 215, a random access memory (RAM) 203, a network interface device 212, an operation interface 214 such as a universal serial bus (USB) and a memory such as a hard disk drive or a solid state drive (SSD) 207. Preferably, the computer or console 200' includes a display 209. The computer 200' may connect with a rotary junction, the motor PM, the motor SM, and/or one or more other components of a system (e.g., the system 100, the system 100', the system 100", the system 100''', etc.) via the operation interface 214 or the network interface 212. A computer, such as the computer 200, 200', may include the RJ, PM and/or the SM in one or more embodiments. The operation interface 214 is connected with an operation unit such as a mouse device 211, a keyboard 210 or a touch panel device. The computer 200' may include two or more of each component. Alternatively, the CPU 201 or the GPU 215 may be replaced by the field-programmable gate array (FPGA), the application-specific integrated circuit (ASIC) or other processing unit depending on the design of a computer, such as the computer 200, the computer 200', etc.

A computer program is stored in the SSD 207, and the CPU 201 loads the program onto the RAM 203, and executes the instructions in the program to perform one or more processes described herein, as well as the basic input, output, calculation, memory writing and memory reading processes.

The computer, such as the computer 200, 200', communicates with the PIU 110, the rotary junction (e.g., the RJ, etc.), the motor PM, the motor SM, the catheter 120 and/or one or more other components of a system, such as the system 100, 100', 100", 100''', etc., to perform imaging, and reconstructs an image from the acquired intensity data. The monitor or display 209 displays the reconstructed image, and may display other information about the imaging condition or about an object to be imaged. The monitor 209 also provides a graphical user interface for a user to operate a system (e.g., the system 100, the system 100', the system 100", the system 100''', etc.), for example when performing OCT or other imaging technique, including, but not limited to, reproducing a lumen curve using various criteria. An operation signal is input from the operation unit (e.g., such as, but not limited to, a mouse device 211, a keyboard 210, a touch panel device, etc.) into the operation interface 214 in the computer 200', and corresponding to the operation signal the computer 200' instructs the system (e.g., the system 100, the system 100', the system 100", the system 100''', etc.) to set or change the imaging condition, and to start or end the imaging, and/or to start or end the lumen detection and/or artifact(s) detection. The laser source 101 of an OCT system as aforementioned may have interfaces to communicate with the computers 200, 200' to send and receive the status information and the control signals.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. A non-transitory computer-readable storage medium storing at least one program that operates to cause one or more processors to execute a method for reproducing a curve to a given tolerance in at least one image, the method, executed on the one or more processors, comprising:
   determining a set of original points of the curve that correspond to measurements from an optical imaging device using optical coherence tomography;
   filtering the set of original points using at least one criteria to obtain a subset of original points;
   determining if the subset of original points is less than a predetermined threshold; and
   adjusting the at least one criteria to increase an amount of original points included in the subset of original points when it is determined that the subset of original points is less than the predetermined threshold,
   wherein the at least one criteria is adjusted until it is determined that the subset of original points is equal to or greater than the predetermined threshold.

2. The computer-readable storage medium of claim 1, wherein the curve is a lumen curve.

3. The computer-readable storage medium of claim 1, wherein the optical imaging device is either a catheter or a probe.

4. The computer-readable storage medium of claim 1, wherein the optical imaging device is a catheter that generates the set of original points corresponding to approximately 500 original points of the curve.

5. The computer-readable storage medium of claim 1, further comprising:
   calculating an area of the curve based on the set of original points;
   calculating an area of a new curve based on the subset of original points, when the subset of original points is equal to or greater than the predetermined threshold; and
   comparing the area of the new curve to the area of the curve to determine if the new curve is within the given tolerance.

6. The computer-readable storage medium of claim 5, wherein when the area of the new curve is not within the given tolerance, the at least one criteria is adjusted to increase the amount of original points included in the subset of original points until the area of the new curve is within the given tolerance.

7. The computer-readable storage medium of claim 1, wherein the at least one criteria is one of a point-to-point distance, a local curvature and a quality of measurement.

8. The computer-readable storage medium of claim 1, wherein the at least one criteria is selected based on a type of optical imaging device used to obtain the set of original points.

9. The computer-readable storage medium of claim 1, wherein a quantity of original points of the predetermined threshold corresponds to a type of curve being reproduced.

10. The computer-readable storage medium of claim 9, wherein the type of curve being reproduced is a circle and a cubic-spline curve technique is used to determine that the predetermined threshold is 8 original points.

11. The computer-readable storage medium of claim 1, wherein the given tolerance is based on at least one of an area of the curve, a perimeter of the curve, a root-mean-square (RMS) of point-to-point differences of the curve.

12. The computer-readable storage medium of claim 1, wherein the at least one image is generated from a multi-modality optical coherence tomography (MM-OCT) imaging apparatus and the at least one criteria is a point-to-point distance.

13. The computer-readable storage medium of claim 12, wherein the filtering of the set of original points further comprises:
   obtaining parameter values including a separation base, a separation multiplier and a minimum point count, wherein the separation base multiplied by the separation multiplier represents a minimum distance apart between two points for the subset of original points that are selected from the set of original points using the obtained parameter values,
   wherein the minimum point count represents the predetermined threshold.

14. The computer-readable storage medium of claim 13, wherein when the subset of original points is less than the minimum point count, the separation multiplier is decremented until a new subset of original points is greater than the minimum point count or the separation multiplier is equal to 1.

15. The computer-readable storage medium of claim 13, wherein when the subset of original points is equal to or greater than the minimum point count, it is determined whether an area of a new curve is within the given tolerance when compared to an area of the original curve and when the area of the new curve is not within the given tolerance, the separation multiplier is decremented until the area of the new curve is within the given tolerance or the separation multiplier is equal to 1.

16. The computer-readable storage medium of claim 1, wherein the at least one criteria is a local curvature and the filtering of the set of original points further comprises:
   setting a minimum curvature value;
   obtaining the subset of original points based on the minimum curvature value; and
   calculating for each set of 3 contiguous points from the subset of original points, a curvature at a center point and determining whether the curvature at the center point is greater than the minimum curvature, when the curvature at the center point is greater than the minimum curvature, the center point is added to a new curve,
   wherein, when it is determined that the subset of original points is less than the predetermined threshold and the minimum curvature value is not equal to one, the at least one criteria is adjusted by decrementing the minimum curvature value until the subset of original points is not less than the predetermined threshold or the minimum curvature value is equal to one.

17. An apparatus for reproducing a curve to a given tolerance in at least one image, the apparatus comprising:
one or more processors; and
one or more non-transitory computer readable storage memories including instructions that, when executed by the one or more processors, cause the apparatus to:
determine a set of original points of the curve that correspond to measurements from an optical imaging device, using optical coherence tomography;
filter the set of original points using at least one criteria to obtain a subset of original points;
determine if the subset of original points is less than a predetermined threshold; and
adjust the at least one criteria to increase an amount of original points included in the subset of original points when it is determined that the subset of original points is less than the predetermined threshold,
wherein the at least one criteria is adjusted until it is determined that the subset of original points is equal to or greater than the predetermined threshold.

18. A non-transitory computer-readable storage medium storing at least one program that operates to cause one or more processors to execute a method for reproducing a curve to a given tolerance in at least one image, the method, executed on the one or more processors, comprising:
determining a set of original points of the curve that correspond to measurements from an optical imaging device, using optical coherence tomography;
filtering the set of original points using quality of measurement as a criteria to obtain a subset of original points by finding a minimum measurement quality value and a maximum measurement quality value from the set of original points of the curve and adding each point from the set of original points that has a value that is greater than or equal to the minimum measurement quality value to the subset of original points;
determining if the subset of original points is less than a predetermined threshold; and
adjusting the quality of measurement to increase an amount of original points included in the subset of original points when it is determined that the subset of original points is less than the predetermined threshold and the minimum measurement quality value is not less than a quality limit,
wherein the minimum measurement quality value is adjusted by a delta quality until it is determined that the subset of original points is equal to or greater than the predetermined threshold or the minimum measurement quality value is less than the quality limit.

19. The computer-readable storage medium of claim 18, wherein the delta quality is computed by multiplying 0.1 by the difference between the maximum measurement quality value and the minimum measurement quality value, and wherein the quality limit is set to the minimum measurement quality value.

* * * * *